United States Patent [19]

Gessner

[11] Patent Number: 5,294,482

[45] Date of Patent: * Mar. 15, 1994

[54] STRONG NONWOVEN FABRIC LAMINATES FROM ENGINEERED MULTICONSTITUENT FIBERS

[75] Inventor: Scott L. Gessner, Greenville, S.C.

[73] Assignee: Fiberweb North America, Inc., Simpsonville, S.C.

[ * ] Notice: The portion of the term of this patent subsequent to Oct. 30, 2007 has been disclaimed.

[21] Appl. No.: 784,967

[22] Filed: Oct. 30, 1991

Related U.S. Application Data

[63] Continuation of Ser. No. 344,744, Apr. 28, 1989, Pat. No. 5,108,827.

[51] Int. Cl.⁵ .................... B32B 27/34; B32B 27/36; D04H 1/04; D02G 3/00
[52] U.S. Cl. .................... 428/287; 428/284; 428/286; 428/288; 428/296; 428/298; 428/373; 428/374; 428/903
[58] Field of Search ............... 428/171, 198, 296, 284, 428/903, 373, 287, 286, 288, 298, 374

[56] References Cited

U.S. PATENT DOCUMENTS

| | | | |
|---|---|---|---|
| 4,196,245 | 4/1980 | Kitson et al. | 428/284 |
| 4,632,861 | 12/1986 | Vassilatos . | |
| 4,766,029 | 8/1988 | Brock et al. . | |
| 4,818,597 | 4/1989 | Da Ponte et al. | 428/284 |
| 4,830,904 | 5/1989 | Gessner et al. | 428/373 |
| 4,837,067 | 6/1989 | Govey, Jr. et al. | 428/288 |
| 4,839,228 | 6/1989 | Jezic et al. | 428/401 |
| 4,863,785 | 9/1989 | Berman et al. . | |
| 4,908,052 | 3/1990 | Largman et al. | 428/373 |
| 4,988,560 | 1/1991 | Meyer et al. | 428/296 |

FOREIGN PATENT DOCUMENTS

340982 11/1989 European Pat. Off. .
405793 1/1991 European Pat. Off. .
416620 3/1991 European Pat. Off. .

*Primary Examiner*—James D. Withers
*Attorney, Agent, or Firm*—Bell, Seltzer, Park & Gibson

[57] ABSTRACT

The present invention provides a thermally-bonded nonwoven fabric that is made from a web which comprises from 100 to 5 percent by weight of multiconstituent fibers. The multiconstituent fibers are composed of highly dispersed blends of at least two different immiscible thermoplastic polymers and have a dominant continuous polymer phase with at least one noncontinuous phase dispersed therein. The noncontinuous phase exists as an elongated fibrillar polymer domain oriented generally in the direction of the fiber axis. No single polymer domain cross-section of the noncontinuous phase or phases is larger than 0.1% of the cross-sectional area of the fiber. The polymer of the noncontinuous phase or phases has a Polymer Melt Temperature (PMT) at least 30° C. below the PMT of the continuous phase. The fiber is configured such that the noncontinuous phase or phases occupy a substantial portion of the fiber surface. In addition to such fabrics, laminates—made by combining nonwoven fabrics made from the materials and processes as described herein with films, paper, tissue, woven fabrics, or nonwoven fabrics such as meltblowns—are also contemplated. The fabric according to the invention readily bonds to other materials of the sorts mentioned, and is therefore suitable for use in filtration media, medical and clean room garments, CSR wrap, absorbent article backsheets, and other barrier structures.

44 Claims, 2 Drawing Sheets

STRONG NONWOVEN FABRIC LAMINATES FROM ENGINEERED MULTICONSTITUENT FIBERS

This application is a continuation of application Ser. No. 07/344,744, filed on Apr. 28, 1989, now U.S. Pat. No. 5,108,827.

BACKGROUND OF THE INVENTION

1. Field of the Invention

This invention relates to nonwoven fabrics made by thermally bonding fibrous webs made from certain types of multiconstituent fibers, and to laminates incorporating said fabrics. Thermal bonding of the nonwoven fabrics may be accomplished by calender or 'through air' techniques or ultrasonically. The multiconstituent fibrous webs may contain other fibers in addition to the thermoplastic multiconstituent fibers. The nonwoven fabrics produced according to the present invention may be optimized as to softness and strength characteristics.

2. Description of the Prior Art

Structured multicomponent fibers—made by coextrusion of different polymers in a variety of structured configurations—have long been well-known. Some relevant references are: Davies (U.S. Pat. No. 3,595,731), Gerlach (U.S. Pat. No. 4,361,609), Kiriyama (U.S. Pat. No. 4,568,506), and Uchikawa (U.S. Pat. No. 4,770,925).

A few references cite fibers and nonwoven fabrics made from polymer blends wherein the dominant continuous phase is lower melting than is the dispersed noncontinuous phase; see Kubo (European Patent Application No. 0277707), Wincklhofer (U.S. Pat. No. 3,620,892) and Vassilatos (U.S. Pat. No. 4,632,861). By definition, to thermally bond such fibers, portions of the continuous fiber phase are raised to temperatures where partial molecular relaxation of the continuous lower melting phase occurs. Relaxation occurs not only at the bond sight proper but also in the fiber region surrounding the bond sight which is responsible for distributing a load or strain throughout the bonded fiber network. Although thermally-bonded nonwoven fabrics can be made from these materials, strength is compromised.

Some instances are also known wherein blends of different polymers are extruded from the orifices of spinnerets in order to make fibers containing "free form" microfibrils which can then be separated from the matrix polymer: Breen (U.S. Pat. No. 3,382,305), Twilley (U.S. Pat. No. 3,369,057), and Allan (U.S. patent application Ser. No. 07/220,203), now abandoned.

Finally, Graham (U.S. Pat. No. 4,769,279) refers to meltblown fibers and fabrics made from blends of ethylene/acrylic copolymer with a second fiber-forming polymer such as a polyvinyl, a polyamide, and a polyolefin. Graham does not disclose thermally-bonded nonwoven fabrics from engineered fibers, however. Furthermore, the Graham disclosure is limited to blends based upon low viscosity ethylene/acrylic copolymers.

SUMMARY OF THE INVENTION

The present invention provides nonwoven fabrics made of engineered multiconstituent fibers. By "engineered" fibers, we mean oriented fibers made by melt-spinning blends of two or more immiscible polymers that are highly dispersed and that contain a dominant continuous phase which is substantially higher in melting point than the discontinuous phase or phases.

The present invention provides a thermally-bonded nonwoven fabric having a basis weight in the range of 5 through 100 g/m$^2$ that is made from a web which comprises from 100 to 5 percent by weight of a multiconstituent fiber having a fineness of 5 to 50 microns and up to 95 percent by weight of other fibers. Said multiconstituent fiber is composed of a highly dispersed blend of at least two different immiscible thermoplastic polymers and has a dominant continuous polymer phase and at least one noncontinuous phase dispersed therein. The noncontinuous phase exists as an elongated fibrillar polymer domain oriented generally in the direction of the fiber axis. The mean of the polymer domain cross-sections of said noncontinuous phase or phases is less than 0.1% of the cross-sectional area of said fiber. The polymer of the noncontinuous phase or phases has a Polymer Melt Temperature (PMT) at least 30° C. below the PMT of said continuous phase. The fiber is configured such that said noncontinuous phase or phases occupy a substantial portion of the fiber surface.

In addition to the fabrics described above, laminates—made by combining nonwoven fabrics made from the materials and processes as described herein with films, paper, tissue, woven fabrics, or nonwoven fabrics such as meltblowns—are also contemplated. The fabric according to the invention readily bonds to other materials of the sorts mentioned, and is therefore suitable for use in filtration media, medical and clean room garments, CSR wrap, absorbent article backsheets, and other barrier structures.

DESCRIPTION OF THE PREFERRED EMBODIMENTS

Biconstituent or multiconstituent fibers that may be used to make fabrics according to the present invention are those which are spun from an intimately-mixed blend of different polymers in which at least two of the polymers in the blend are immiscible. The choice of polymers is limited to those that are thermoplastic (including many elastomers) and that have a melt temperature below 350° C., preferably below 275° C. Examples of polymers that can be used are:

Polyethylenes:
Low density PE (0.90–0.940 g/cc)
Long-chain branched PE
LLDPE (made with $C_3$–$C_{10}$ alpha-1-olefin copolymers or 4-methyl-1-pentene)
Medium and high density PE (0.940–0.960 g/cc)
Homopolymer or with copolymers described above
Atactic polypropylene
Polypropylene (at least 90% isotactic)
Block copolymers of ethylene and propylene
Random copolymers of ethylene and propylene
Polybutylene
Poly(4-methyl-1-pentene) [TPX]
Polycarbonate
Polyesters, e.g. poly(oxyethyleneoxyterephthaloyl)
Polyamides, e.g. poly(imino-1-oxohexamethylene) [Nylon 6] and poly(iminohexamethyleneiminoadipoyl) [Nylon 66]

Poly(oxymethylene)
Polystyrene
Styrene copolymers, e.g. styrene acrylonitrile [SAN]
Polyphenylene ether
Polyphenylene Oxide [PPO]
Polyetheretherketone [PEEK]
Polyetherimide
Polyphenylene Sulfide [PPS]
Poly(vinyl acetate) [PVA]
Poly(methyl methacrylate) [PMMA]
Poly(methacrylate) [PMA]
Ethylene acrylic acid copolymer
Polysulfone The biconstituent or multiconstituent fibers that make up a significant portion of the webs to be thermally bonded according to the present invention must exhibit a high degree of dispersion. In principle, the mean of the cross-sectional areas of the noncontinuous phase or phases is less than 1/1000th of the cross-sectional area of the fiber. Factors which determine the level of dispersion and phase morphology of the dispersed phase or phases in blend fibers are discussed in detail by D. R. Paul in "Polymer Blends", volume 2, chapter 16. Briefly, the dispersed-phase morphology of the blend fiber is dependent upon the relative rheologies of the blend components, the interfacial tension between the two or more phases, the polymer volume ratio, and the three stages of the blend melt preparation and processing: melt dispersion, extrusion, and extrudate drawdown prior to solidification. In general, the largest domains in the blend will exist when the polymer ratio is near 1.0; at this point the polymers are nearly co-continuous. The domain size of the discontinuous phase will decrease as the ratio deviates from 1.0, given that the quantity of work 'mixed' into the blend and the melt-spinning conditions remain constant.

Thermal bonding work on fabrics made from biconstituent polyethylene/polypropylene staple fibers has demonstrated weak bonding at calender temperatures at and just above the melting point of the lower melting polyethylene constituent. One of the problems with biconstituents in general in thermal bonding can be that the lower melting component is distributed throughout the fiber matrix rather than being concentrated at the surface where it can be active in bonding. Therefore fibers according to the present invention are often preferably fibers with increased surface-to-volume ratios, with the ultimate being a ribbon-shaped fiber. High surface/volume fibers make more of the lower melting component available for bonding, which ultimately results in higher tensile strength fabrics and laminates.

Figure 1:
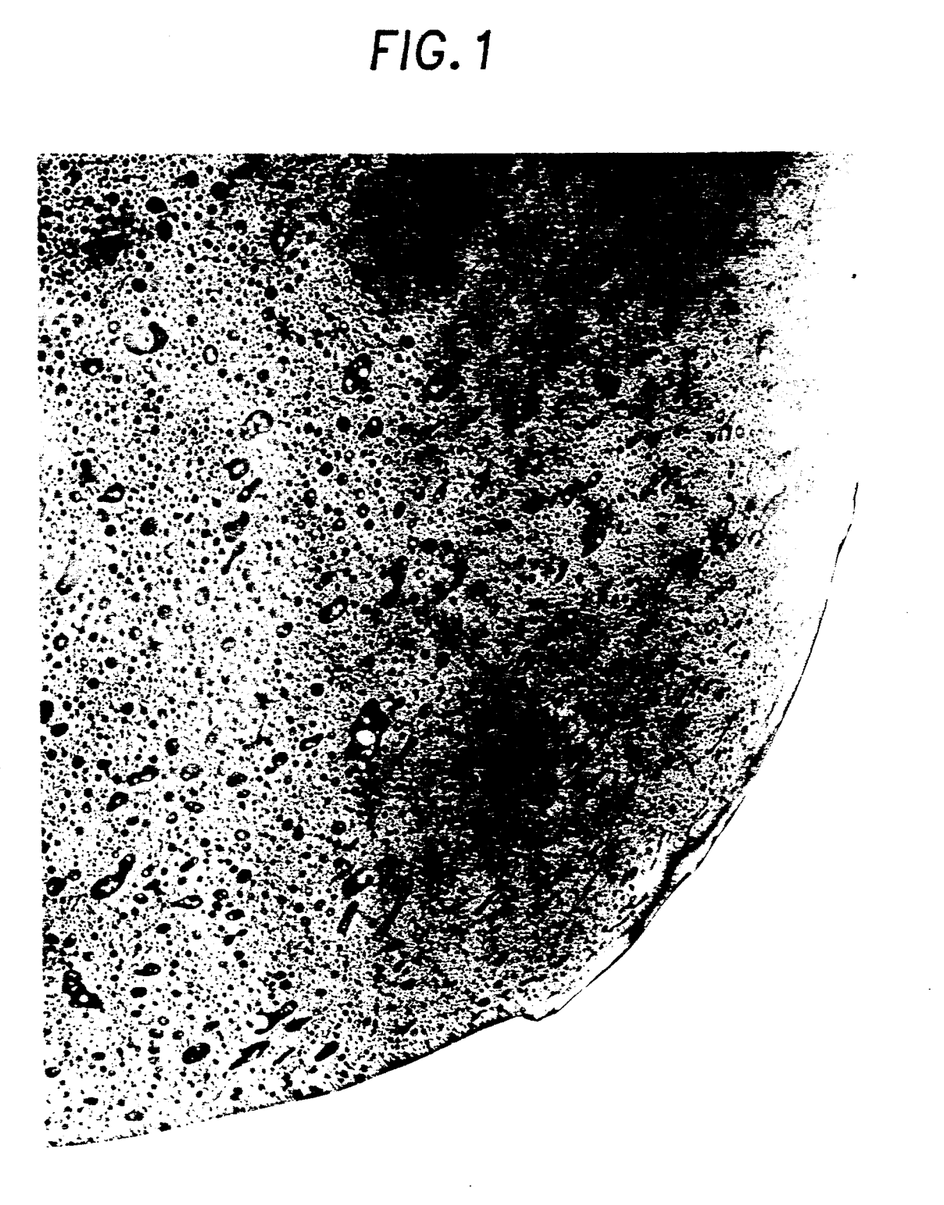
FIG. 1 is a photomicrograph of a cross-section of a 20-micron-diameter fiber enlarged 25,000 times.

FIG. 1 is a TEM photomicrograph of a $RuO_4$-stained polyethylene/polypropylene fiber cross-section, enlarged 25,000 times. The dark domains are polyethylene (PE); the lighter domains are the continuous polypropylene (PP) phase. The photograph demonstrates how well the PE phase is dispersed in the PP phase. It is interesting to note how the PE phases become circumferentially elongated at the fiber surface.

Fibers used to make fabric in accordance with the present invention may be processed as follows: two or more polymers, selected to meet the melting point differential that characterizes the present invention, are combined and blended to form a dispersion. The dispersion is then either melt-spun into fibers, which may be formed into webs for instance by carding, airlaying, or wetlaying, or melt-spun directly into fibrous webs by a spunbonding process. The webs are then thermally-bonded to transform them into strong soft biconstituent-fiber nonwoven fabrics. The specific fabric characteristics will be dependent on the choice of precursor fiber and processing conditions. Said nonwoven fabrics may then be laminated into structures having a variety of desirable end-use characteristics.

Appropriate combinations of polymers combined to make the fibers used in accordance with the present invention are intimately blended before being melt-spun into fibers or fibrous webs. A high degree of mixing is necessary in order to prepare blends that will satisfy the degree of dispersion criteria that characterizes the fibers used according to the present invention. Among the commercially available mixers that can be used are the Barmag 3DD three-dimensional dynamic mixer supplied by Barmag AG of West Germany and the RAPRA CTM cavity-transfer mixer supplied by the Rubber and Plastics Research Association of Great Britain.

An example of an immiscible blend according to the present invention is a supermixed blend of linear low density polyethylene with polypropylene.

Thermally-bonded nonwoven fabrics according to the present invention exhibit advantages over similar homofilament-based nonwovens. A few of those advantages are higher tensile strength/basis weight ratio, and higher tear resistance/basis weight ratio. Many of these advantages are made possible by the fact that the lower melting component of the fibers used according to the present invention effects bonding at conditions that do not cause 'relaxation' or loss of molecular orientation of the higher melting component. Typically, fiber used for thermally-bonded coverstock is not highly oriented. Highly oriented polypropylene, for example, is difficult to bond thermally without loss of molecular orientation in the individual filament. In addition, fabrics made from highly drawn polypropylene are harsh and possess poor 'hand'. The filaments described by the present invention can be highly drawn to impart high tenacities and then thermally bonded into a nonwoven fabric with essentially no loss of individual filament tenacity. The retention of individual filament tenacity improves the strength properties of the fabric. Selection of the appropriate polymer (polyethylene for example) as the bonding constituent yields a fabric with greater softness than its homofilament counterpart.

The process for manufacturing the webs to be thermally or sonically bonded according to the present invention can be any of the known commercial processes for making nonwoven fabrics, including processes that use mechanical, electrical, pneumatic, or hydrodynamic means for assembling fibers into a web, for example carding, wetlaying, carding/hydroentangling, wetlaying/hydroentangling, and spunbonding.

EXAMPLE 1

Biconstituent staple fiber was prepared by dry blending 40% by weight of an ethylene/1-octene linear low density polyethylene [LLDPE] having a melt index of 26.5 and a density of 0.940 grams/cc with 60% by weight of controlled rheology polypropylene [PP] having a melt flow rate of 26. The dry blend [PP/LLDPE] was fed into a single-screw extrusion system equipped with a Barmag 3DD intensive mixer. Filaments were extruded and drawn to a final denier per filament of approximately 2.0. Line speeds and cold draw ratios were adjusted to produce two filament samples, one having 2X cold draw and another having 3.5X draw.

Refer to Table I, samples 8319-2 and 8319-3, respectively.

Figure 2:
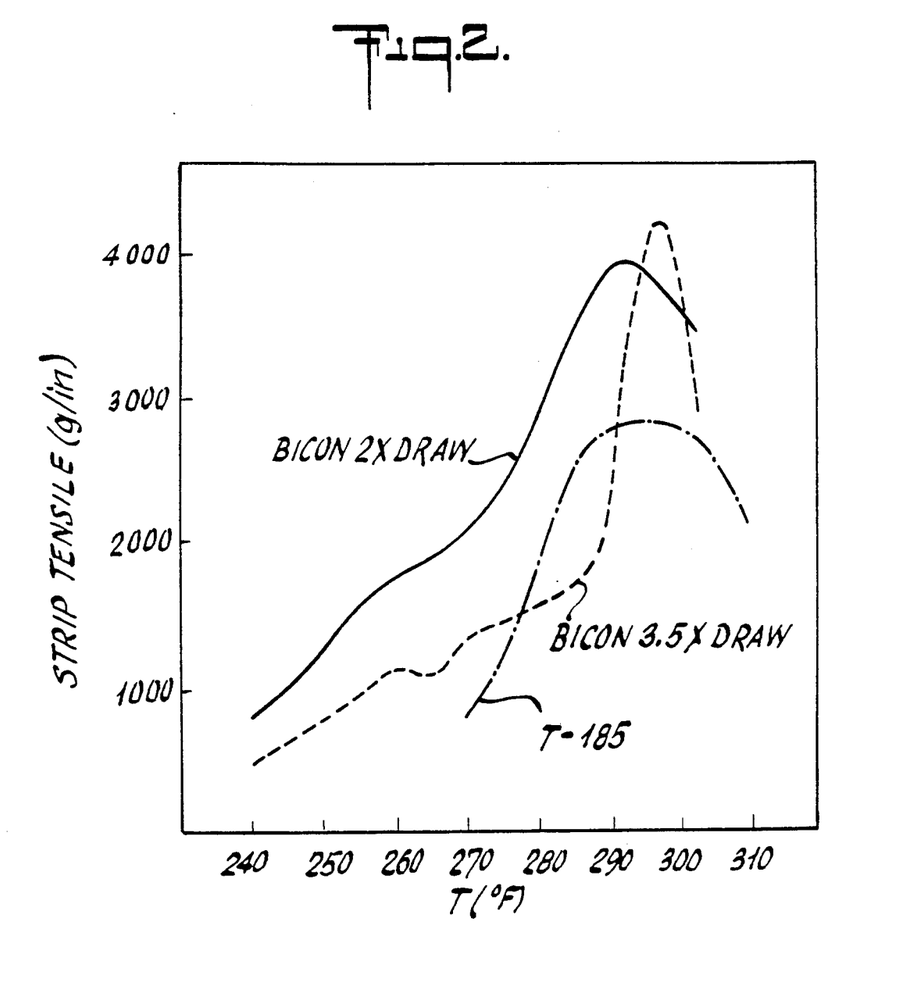
FIG. 2 is a graphic comparison of tensile strengths versus temperature for various fibers.

One gram samples of each-fiber type were formed into a web using a lab-scale carding device. The carded webs were then bonded on a Beloit-Wheeler lab top calender using a 16%-diamond-bond pattern and a nip pressure of approximately 400 PLI. Strip tensile strengths were determined for samples bonded over a range of temperatures. Carded webs made from Hercules T-185 polypropylene fiber served as a control. The biconstituent-based fabrics demonstrate superior tensile properties over the polypropylene homofilament-based fabric (see Tables II, III, and IV, and FIG. 2).

EXAMPLE 2

Both polypropylene and PP/LLDPE dry blend samples were (separately) fed into a single-screw extrusion system equipped with a Barmag 3DD intensive mixer. Filaments were extruded and drawn to a final denier per filament of approximately 2.0. Line speeds and cold draw ratios were adjusted to produce filament samples having 2X draw. Refer to Table I, samples 8319-1A and 8319-2, respectively.

Each fiber sample was separately carded and thermally bonded on a 36-inch-wide semicommercial line. Physical properties were then determined for the fabric samples. Data in Table V. The biconstituent fiber-based fabrics exhibited superior strip and grab tensiles, energies at yield (TEA), and tear values.

EXAMPLE 3

Staple biconstituent fiber containing 1% by weight of a substituted-sorbitol nucleating agent was prepared from dry blends of PP/LLDPE that was fed into a single-screw extrusion system equipped with a Barmag 3DD intensive mixer. Filaments were extruded and drawn to a final denier per filament of approximately 2.0. Line speeds and cold draw ratios were adjusted to produce filament samples having 3.5X draw. Refer to Table I, sample 8319-7.

The fiber was carded and thermally bonded on a 36-inch-wide semicommercial line. Data in Table VI. The strip and grab tensiles, energies at yield, and tear values were superior to a similar fiber sample without nucleating agent.

EXAMPLE 4

Biconstituent fiber 8342 was prepared from a dry blend of 40% by weight of an ethylene/1-octene copolymer [LLDPE] having a melt index of 50 and a density of 0.925 g/cc with 60% by weight of controlled rheology polypropylene [PP] having a melt flow of 35. Multiconstituent fiber 8343 was prepared from a dry blend of 40% by weight LLDPE having a melt index of 50 and a density of 0.925 g/cc with 55% by weight of controlled rheology PP having a melt flow of 35 and with 5% by weight of ethylene/acrylic acid copolymer [EAA] composed of low density polyethylene having a melt index of 300 and an acrylic acid content of 20%. Melt blends were then separately prepared and extruded and pelletized using a single screw extruder equipped with a 6 row Rapra cavity-transfer mixer (CTM) and a strand die cutter. The polymer-blend pellets were then separately re-extruded into filaments and melt-drawn to a final denier per filament of 1.9 and 2.7, respectively.

One gram samples of each fiber type were formed into webs, bonded, and tested as described in Example 1. Filament and fabric tensile properties are indicated in Table VII.

END-USE EXAMPLES

EXAMPLE 5

8350-1A: PE film to PE/PP bicon fabric 8326-03 (1 osy)

8350-1B: PE film to PP fabric 8326-02 (1 osy)

To demonstrate the ability Of multiconstituent fabric to form a fabric/film laminate, five-inch-wide fabric samples of a thermally bonded multiconstituent fiber-based nonwoven fabrics were 'heat sealed' to polyethylene film. Laminate samples were prepared by heat-sealing a sandwich structure composed of carded fabric (8326-02 and 8326-03) (bottom)/polyethylene film (middle)/cover fabric (8326-02) (top). The cover fabric was used to insulate the low melting film from the sealing die. Fabric and film dimensions were 5"×12". Time, pressure, and die-temperature conditions were chosen that insured optimum adhesion of the fabric to the film while maintaining the film integrity. The heat sealer used was a Hut-Theller Precision Instruments West, Model EB (Petaluma, Calif.). Multiple heat-sealed samples were prepared by sealing across the width of the laminate sample. The die dimensions were flat, ⅜"×5", or 1.875 square inches.

Peel strengths were determined relative to a homofil fabric laminate control. Peel strengths are indicative of the level of adhesion between the fabric and film layers of the laminate. Peel strengths were determined using an Instron Model 4201 tensile tester. Strips 1-inch wide were cut from each sealed sample. The fabric was placed in the upper grip of the tensile tester and the film in the lower grip. A gauge length of 3-inches and a cross-head speed of 5-inches/minute were used. Peel strength properties are indicated in Table VIII. The level of adhesion was greater for the laminate which contained the multiconstituent fiber.

Examples 6 and 7 relate to breathable liquid barrier laminates with textile-like hand. Such laminates are suitable for use but not limited to use as medical and industrial garments, CSR wrap, surgical drape, and housewrap. The laminates are prepared from a layer or layers of microfibrous (for example meltblown) polymer, such as polypropylene, sandwiched between two layers of nonwoven fabric containing multiconstituent fiber according to the present invention. The discontinuous polymer phase of the multiconstituent fiber occupies a portion of the surface of the fiber such that both polymers of the blend are available for thermal or sonic bonding and/or lamination. The fabric can be bonded prior to lamination or can be directly deposited on either side of the microfibrous layer just prior to lamination.

The microfibrous layer can be composed of meltblown fibers, wet laid pulps, or webs prepared by other known means. The microfibrous layer can be formed prior to the lamination or extruded or formed directly onto the multiconstituent nonwoven fabric prior to lamination. The microfibrous layer must be composed of a polymer which adheres to either the continuous or discontinuous polymer component of the multiconstituent fiber upon thermal or sonic lamination.

Thus for instance, high melt flow isotactic polypropylene could be meltblown into a microfibrous web and then laminated to a fabric made from a polymer-blend fiber having polypropylene as one of the polymer constituents. Lamination can be with known calendering or sonic bonding technology. Bond pattern and processing conditions can be tailored to impart the desired combination of strength, barrier, drape, and textile aesthetics.

EXAMPLE 6

Samples of flat-calendered 'sandwich-type' laminates were prepared from a polypropylene meltblown web weighing 20 grams per square meter and having a nominal filament diameter of 5 microns and two outer nonwoven layers composed of a multiconstituent fiber-based nonwoven fabric like that described in Example 1 and identified as Sample No. 8326-03 in Table V. The three webs were simultaneously unwound from a backstand and fed continuously into a heated calender nip. The lamination was effected using a 22" lab calender equipped with a heated smooth rubber roll and a heated smooth steel roll. The samples were prepared at varied calender roll surface temperatures, ranging from 318° F. to 306° F. for the steel roll and from 300° F. to 284° F., for the rubber roll. Nip pressure was held constant at 150 pounds per linear inch (pli), and line speed was held constant at 22 feet per minute.

Physical properties were determined for the resulting laminate samples and are identified as sample numbers 8331-1A through 8331-1F in Table IX. It is apparent from these data (8331-1A through 8331-1F) that a breathable liquid-barrier laminate can be obtained with excellent fabric tenacity.

EXAMPLE 7

A helically-bonded 'sandwich-type' laminate was prepared by a procedure similar to that described in Example 6, but wherein the smooth rolls were replaced with steel rolls engraved with a diagonal line pattern such that the angle between the crisscross bond lines of the diagonal bonds opening in the machine direction (MD) measures 120 degrees, each line measuring 60 degrees off the MD axis and such that the raised bonding surfaces of each roll are flat and approximately 1 mm wide, separated by a recessed area measuring approximately 1.5 mm wide. A laminate fabric was produced at 22 fpm, 150 pli, at a calender roll surface temperature of 290° F. to 294° F.

Physical properties were determined for the fabric which is identified as sample number 8331-04 in Table IX. It is apparent from a comparison of the thickness, tensile, and barrier properties of this fabric with those in the same Table which have been flat-calendered that significantly different properties can be obtained for laminates composed of identical starting materials. Thickness is greatly increased over the flat-calendered samples. The loft of a fibrous web contributes to its ability to filter airborne or liquidborne particles efficiently. Air permeability is equivalent to breathability, a property associated with comfort in disposable garments. Air permeability combined with liquid barrier properties defines a fabric which can be used as a protective garment in a medical or industrial end use. In addition, the range of properties exhibited by these laminates demonstrate the flexibility of multiconstituent fabrics in laminate applications.

EXAMPLE 8

By use of the isotactic polypropylene/linear low density polyethylene polymer blend fiber-based fabric described in Table V (Sample No. 8326-04C), laminates were prepared that demonstrate the flexible bonding character of these novel substrates. Film and meltblown fabric were acquired whose polymer compositions matched either that of the continuous phase or that of the noncontinuous phase of the polymer-blend fiber. The grades of each polymer were selected that suited the respective substrate manufacturing processes, and are therefore not the identical polymers used in the manufacture of the multiconstituent fiber. 'Sandwich-type' laminates were prepared using the procedure described in Example 7.

Physical property data appears in Table X. It is apparent from examination of this data that laminates exhibiting excellent tensile and barrier properties can be prepared by bonding the multiconstituent fiber-based fabric to substrates composed of a polymer selected from the same polymer groups represented in the multiconstituent fiber.

From the above description and specific Examples of the invention, many variation in the webs, composites, useful products, and processes of this invention will be apparent to those skilled in the relevant arts. Such variations are within the scope of the present invention as measure by the apended claims.

TABLE I

| DB # | POLYBLEND FIBER DESCRIPTION | BICONSTITUENT FILAMENT PROPERTIES | | | |
|---|---|---|---|---|---|
| | | COLD DRAW RATIO | DENIER PER FILAMENT | FILAMENT TENACITY (g/den) | ELONGATION AT BREAK (%) |
| 8319-1A | HIMONT Z30S PP | 2.2 | 2.10 | 3.12 | 51 |
| | | | (.10) | (.12) | (9.4) |
| 8319-1B | HIMONT Z30S PP | 3.5 | 1.95 | 4.72 | 27 |
| | | | (.10) | (.39) | (3.7) |
| 8319-2 | 40/60 PE (a)/PP | 2 | 1.96 | 2.04 | 95 |
| | | | (.11) | (.09) | (40) |
| 8319-3 | 40/60 PE (a)/PP | 3.5 | 1.98 | 3.29 | 33 |
| | | | (.11) | (.39) | (7) |
| 8319-4 | 40/60 PE (b)/PP | 2 | 2.00 | 2.39 | 128 |
| | | | (.10) | (.11) | (32) |
| 8319-5 | 40/60 PE (b)/PP | 3.5 | 1.99 | 3.98 | 39 |
| | | | (.12) | (.20) | (4.8) |
| 8319-6 | PE (a)/PP + .5% NA | 2 | 1.96 | 1.85 | 59 |
| | | | (.12) | (.08) | (18.6) |
| 8319-7 | PE (a)/PP + .5% NA | 3.5 | 1.94 | 3.75 | 35 |

TABLE I-continued

| DB # | POLYBLEND FIBER DESCRIPTION | BICONSTITUENT FILAMENT PROPERTIES | | | |
|---|---|---|---|---|---|
| | | COLD DRAW RATIO | DENIER PER FILAMENT | FILAMENT TENACITY (g/den) | ELONGATION AT BREAK (%) |
| | | (.10) | (.17) | (5.3) | |

(#) - DENOTES STANDARD DEVIATION, WHERE n = 10.
PE (a) - DOW ASPUN (R) 6811, octene-1/ethylene copolymer, MI = 26
PE (b) - DOW ASPUN (R) 6815, octene-1/ethylene copolymer, MI = 12
PP - HIMONT Z30S Controlled Rheology Grade Polypropylene, MF = 26
NA - MILAD 5L71-10 Nucleating Agent. 10% conc. in LLDPE

LAB TOP FABRIC PROPERTIES OF BICONSTITUENT BASED THERMAL BOND FABRICS

TABLE II (FIBER: 40/60 PE/PP, 8319-2, 2X DRAW, TABLE I)

| DATA BOOK # | CALENDER SURFACE TEMPERATURE | | STRIP TENSILE | | | TEA (in/g/in2) |
|---|---|---|---|---|---|---|
| | EMB. F. | SM. F. | (g/in) | SD | % E | |
| 8324-1 | 240 | 244 | 819 | 87 | 11 | 116 |
| 2 | 250 | 254 | 1263 | 55 | 17 | 224 |
| 3 | 255 | 259 | 1811 | 86 | 15 | 317 |
| 4 | 260 | 264 | 1594 | 48 | 19 | 302 |
| 5 | 265 | 269 | 1817 | 185 | 20 | 347 |
| 6 | 270 | 274 | 2058 | 184 | 22 | 451 |
| 7 | 275 | 279 | 2292 | 100 | 23 | 484 |
| 8 | 280 | 284 | 2829 | 141 | 21 | 554 |
| 9 | 289 | 285 | 3571 | 177 | 28 | 821 |
| 10 | 294 | 290 | 3938 | 215 | 27 | 804 |
| 11 | 299 | 295 | 3747 | 355 | 32 | 930 |
| 12 | 305 | 300 | 3360 | 272 | 27 | 686 |

TABLE III (FIBER: 40/60 PE/PP, 8319-3, 3.5X DRAW, TABLE I)

| 8324-13 | 240 | 245 | 469 | 53 | 6 | 49 |
|---|---|---|---|---|---|---|
| 14 | 245 | 249 | 625 | 42 | 9 | 78 |
| 15 | 250 | 254 | 765 | 52 | 9 | 100 |
| 16 | 255 | 259 | 977 | 58 | 9 | 123 |
| 17 | 260 | 264 | 1115 | 216 | 10 | 153 |
| 18 | 265 | 269 | 1067 | 185 | 7 | 128 |
| 19 | 270 | 274 | 1351 | 186 | 9 | 164 |
| 20 | 275 | 279 | 1368 | 93 | 8 | 158 |
| 21 | 280 | 284 | 1568 | 147 | 7 | 182 |
| 22 | 289 | 285 | 1868 | 121 | 12 | 247 |
| 23 | 294 | 290 | 3230 | 173 | 11 | 381 |
| 24 | 299 | 295 | 4228 | 181 | 14 | 559 |
| 25 | 305 | 300 | 2704 | 211 | 26 | 644 |

TABLE IV (FIBER: HERCULES T-185)

| 8324-26 | 270 | 265 | 834 | 29 | 20 | 196 |
|---|---|---|---|---|---|---|
| 27 | 280 | 275 | 1611 | 103 | 33 | 573 |
| 28 | 290 | 285 | 2705 | 51 | 73 | 1757 |
| 29 | 300 | 295 | 2809 | 361 | 54 | 1289 |
| 30 | 310 | 305 | 2136 | 95 | 14 | 232 |

NOTES: ALL SAMPLES PRODUCED AT 500 PLI, 22 FPM, 18% BOND AREA

TABLE V

PHYSICAL PROPERTIES OF SELECTED STAPLE BICONSTITUENTS

| DATABOOK # | FIBER SAMPLE IDENTIFICATION (TABLE I) | FIBER DENIER (dpf) | CALENDER SURFACE °F. E/S | B.W. (gsy) | LOFT (mils) | STRIP TENSILES MD* (losy) (g/in) | % E | TEA |
|---|---|---|---|---|---|---|---|---|
| 8326-02 | PP FIBER 8319-1 | 2 | 270/300 | 28.8 | 15.9 | 1124 | 35 | 164 |
| 8326-03 | FIBER 8319-2, 2X | 1.95 | 270/295 | 32.6 | 13.4 | 2098 | 24 | 415 |
| 8326-04C | SAME AS ABOVE | 1.95 | 300/300 | 31.6 | 13.3 | 1972 | 14 | 207 |

| DATABOOK # | STRIP TENSILES CD* (losy) (g/in) | % E | TEA | GRAB TENSILES MD (lbs) | % E | CD (lbs) | % E | ELMENDORF TEAR MD (g) | CD (g) | SOFT. (psu) |
|---|---|---|---|---|---|---|---|---|---|---|
| 8326-02 | 288 | 39 | 78 | 4.8 | 16 | 2.1 | 33 | 109 | 144 | 1.7 |
| 8326-03 | 501 | 59 | 256 | 10.5 | 24 | 4.6 | 58 | 138 | 200 | 0.9 |
| 8326-04C | 704 | 40 | 255 | 9.2 | 15 | 6.1 | 46 | 72 | 149 | −0.8 |

TABLE VI

PHYSICAL PROPERTIES OF SELECTED STAPLE BICONSTITUENTS

| DATABOOK # | FIBER SAMPLE IDENTIFICATION (TABLE I) | FIBER DENIER (dpf) | CALENDER SURFACE °F. E/S | B.W. (gsy) | LOFT (mils) | STRIP TENSILES MD* (losy) (g/in) | % E | TEA |
|---|---|---|---|---|---|---|---|---|
| 8326-05 | FIBER 8319-3 | 1.98 | 270/290 | 30.5 | 12.9 | 1293 | 29 | 173 |
| 8326-07 | FIBER 8319-6 | 1.93 | 270/290 | 31 | 14.1 | 1728 | 27 | 262 |

| DATABOOK # | STRIP TENSILES CD* (losy) (g/in) | % E | TEA | GRAB TENSILES MD (lbs) | % E | CD (lbs) | % E | ELMENDORF TEAR MD (g) | CD (g) | SOFT. (psu) |
|---|---|---|---|---|---|---|---|---|---|---|
| 8326-05 | 343 | 43 | 93 | 6.1 | 15 | 2.7 | 32 | 122 | 178 | 0.4 |

TABLE VI-continued
PHYSICAL PROPERTIES OF SELECTED STAPLE BICONSTITUENTS

| | | | | | | | | | | |
|---|---|---|---|---|---|---|---|---|---|---|
| 8326-07 | 464 | 36 | 131 | 8.2 | 18 | 4 | 40 | 178 | 229 | 0.7 |

TABLE VII
FILAMENT AND FABRIC PROPERTIES OF SELECTED MULTICONSTITUENT FIBERS

| Fabric Sample No. (1) | FILAMENT PROPERTIES (1) | | | | FABRIC PROPERTIES (2) | | |
|---|---|---|---|---|---|---|---|
| | (dpf) | Tenacity (gpd) | Elong. (%) | Toughness (gpd) | Tensile (g/in) | Elong. (%) | TEA (in/g/in2) |
| 8342-1 | 1.9 | 1.52 | 420 | 4.5 | 2808 | 74 | 993 |
| STD DEV. | | (0.16) | (61) | (1.0) | (251) | (17) | |
| 8343-1 | 2.7 | 1.0 | 405 | 2.7 | 3276 | 30 | 727 |
| STD DEV. | | (0.21) | (124) | (0.8) | (377) | (6) | |

STD DEV: N = 10
(1) 8342-1 Fabric: melt blend fiber composed of 40:60 wt % PE:PP
8343-1 Fabric: melt blend fiber composed of 40:55:5 wt. % PE:PP:EAA
(2) Fabric properties normalized to 1.0 ounce/yd2 basis weight

TABLE VIII
HEAT SEAL PEEL STRENGTH FOR BICONSTITUENT-FILM LAMINATE

| Sample No. | Peel Strength pk load (g/in) | Elongation at pk (%) | Peel Strength TEA (in/g/in2) |
|---|---|---|---|
| 8350-1A | 559 | 24 | 175 |
| 8350-1B | 443 | 27 | 86 |

Die Geometry: 1" × 5", flat
Time: 500 msec
Temp: top - 245 F.; lower - 245 F.
Pressure: 550 psi

TABLE IX
PE/PP BICONSTITUENT LAMINATES PHYSICAL PROPERTIES

| DB # | SAMPLE DESCRIPTION (1) | B.W. (gsy) | MODEL 549 THICK. (mils) | LAMINATION TEMP. (F.) | STRIP TENSILES (2) MD (g/in) | % E | TEA |
|---|---|---|---|---|---|---|---|
| 8331-1A | FC BICON./PPMB/BICON. | 106 | 11.7 | 318/300 | 9078 | 15 | 1306 |
| 8331-1B | " | 102 | 9.2 | 316/297 | 9340 | 15 | 1078 |
| 8331-1C | " | 90 | 8.5 | 313/294 | 9508 | 16 | 984 |
| 8331-1D | " | 93 | 8.6 | 310/290 | 7963 | 11 | 674 |
| 8331-1E | " | 89 | 8.3 | 308/287 | 9189 | 14 | 855 |
| 8331-1F | " | 96 | 9.2 | 306/284 | 8440 | 14 | 1016 |
| 8331-04 | HELIC. BIC./PPMB/BIC. | 86 | 23.6 | 290/294 | 5863 | 15 | 625 |

| DB # | STRIP TENSILES (2) CD (g/in) | % E | TEA | ELMENDORF TEAR MD (g/in) | CD (g/in) | GURLEY POROSITY (sec) (20 oz) | (5 oz) | HYDRO-STATIC HEAD (cm) | MASON JAR (sec) |
|---|---|---|---|---|---|---|---|---|---|
| 8331-1A | 3940 | 6 | 250 | 360 | 770 | 56 | 275 | 24.1 | 10 |
| 8331-1B | 4286 | 8 | 266 | 325 | 575 | 93 | >5 min. | 25.6 | 70 |
| 8331-1C | 3871 | 8 | 211 | 290 | 490 | 120 | >5 min. | 22.5 | 39 |
| 8331-1D | 4002 | 6 | 194 | 260 | 580 | 66 | >5 min. | 22 | 26 |
| 8331-1E | 4320 | 8 | 224 | 310 | 520 | 65 | >5 min. | 19.6 | 33 |
| 8331-1F | 3796 | 18 | 306 | 320 | 600 | 29 | >5 min. | 18.9 | 28 |
| 8331-04 | 3211 | 17 | 353 | 330 | 460 | inst. | 7 | 13.2 | 3 |

NOTES:
(1) FC - FLAT CALENDERED
HELIC. - CRISSCROSS BOND PATTERN FROM HELICAL ROLLS
PPMB - POLYPROPYLENE MELT BLOWN (20 gsm)
BICON. - POLYETHYLENE/POLYPROPYLENE BICONSTITUENT FIBER BASED FABRIC - 8326-03
(2) TENSILES CORRECTED TO 3 OSY UNIT WEIGHT

TABLE X
PHYSICAL PROPERTIES OF POLYETHYLENE/POLYPROPYLENE BICONSTITUENT FABRIC LAMINATES

| SAMPLE NO. | DESCRIPTION (1) | CALENDER TEMP. (2) (F.) | UNIT WT. (gsy) | (3) CALIPER (mils) | GRAB TENSILES MD (lbs) | El. (%) | CD (lbs) | El. (%) |
|---|---|---|---|---|---|---|---|---|

TABLE X-continued

PHYSICAL PROPERTIES OF
POLYETHYLENE/POLYPROPYLENE
BICONSTITUENT FABRIC LAMINATES

| 8333-05 | BICON/PE FILM/BICON | 252/263 | 76.6 | 28.1 | 22 | 27 | 11.7 | 38 |
|---|---|---|---|---|---|---|---|---|
| 8333-06 | BICON/PP FILM/BICON | 287/288 | 70.9 | 26.4 | 22.7 | 30 | 11.1 | 42 |
| 8333-04 | BICON/PE-MB/BICON | 268/260 | 93.6 | 26.8 | 23.1 | 24 | 10.2 | 34 |
| 8331-04 | BICON/PP-MB/BICON | 290/294 | 86.3 | 27.2 | 25.3 | 25 | 10.8 | 36 |

| SAMPLE NO. | ELM. TEAR MD (g) | ELM. TEAR CD (g) | MULLEN BURST (psi) | (4) GURLEY POROSITY (5 oz) (sec) | (4) GURLEY POROSITY (20 oz) (sec) | (5) MASON JAR (sec) | HYDRO-STATIC HEAD (cm) |
|---|---|---|---|---|---|---|---|
| 8333-05 | 400 | 540 | 21 | NR | 53.3 | 3.16 | 18.4 |
| 8333-06 | 330 | 430 | 19 | NR | 98 | 163 | 23.7 |
| 8333-04 | 350 | 400 | 20 | 1.57 | NR | inst. | 16.1 |
| 8331-04 | 320 | 380 | 19 | 7.1 | NR | 3 | 13.2 |

NOTES:
ALL PE IS 1-OCTENE, LINEAR LOW DENSITY POLYETHYLENE, UNLESS OTHERWISE STATED
(1) BICON - BICONSTITUENT FIBER-BASED FABRIC (8326-04 CARDED THERMALBOND, 40:60, PE:PP), 1 OSY
PE FILM - LOW DENSITY POLYETHYLENE FILM OBTAINED FROM EDISON PLASTIC, 1 MIL.
PP FILM - POLYPROPYLENE FILM OBTAINED FROM EDISON PLASTIC, 1 MIL
PE-MB - POLYETHYLENE MELTBLOWN FABRIC, 20 GSM
(2) CALENDER - HELICAL STEEL/HELICAL STEEL, NIP PRESSURE = 350 PLI, LINE SPEED = 12.5 FPM
(3) FABRIC CALIPER MEASURED USING A 551-M CALIPER TESTER
(4) NR - NO READING, PROCESS EITHER TOO FAST OR TOO SLOW FOR ACCURATE MEASUREMENT
(5) INST - INSTANTANEOUS

I claim:

1. A nonwoven fabric laminate comprising:
a nonwoven web that comprises from 100 to 5 percent by weight of one or more multiconstituent fibers having a fineness of 5 to 50 microns, and from 0 to 95 percent by weight of other fibers;
said multiconstituent fibers being composed of highly dispersed blends of at least different immiscible thermoplastic polymers which are present as a dominant continuous phase and at least one noncontinuous phase dispersed therein, with the polymer of said noncontinuous phase or phases having a Polymer Melting Temperature (PMT) of at least 30° C. below the PMT of said continuous phase, and the mean of the cross-sectional area of said noncontinuous phase or phases being less than 0.1% of the cross-sectional area of said multiconstituent fibers, and said multiconstituent fibers being configured such that said noncontinuous phase of phases occupy a substantial portion of the fiber surfaces;
said web including a multiplicity of thermal bonds bonding the fibers of the nonwoven web; and
at least one other web laminated to said nonwoven web and adhering to the multiconstituent fibers of said nonwoven web.

2. A nonwoven fabric laminate according to claim 1, wherein said at least one other web comprises at least one polyolefin film.

3. A nonwoven fabric laminate according to claim 2, wherein the laminate comprises a diaper backsheet.

4. A nonwoven fabric laminate according to claim 2, wherein said polyolefin film comprises a linear low density polyethylene film.

5. A nonwoven fabric laminate according to claim 1, wherein said thermally bonded nonwoven web consists essentially of from 50 to 5% by weight of said multiconstituent fibers and from 50 to 95% by weight of other textile fibers.

6. A nonwoven fabric laminate according to claim 1, wherein said at least one other web comprises at least one microfibrous layer.

7. A nonwoven fabric laminate according to claim 6, wherein said microfibrous layers is a polyolefin meltblown.

8. A nonwoven fabric laminate according to claim 6, wherein said microfibrous layer is a wetlaid polyolefin synthetic pulp.

9. A nonwoven fabric laminate according to claim 1, wherein said thermally bonded nonwoven web consists essentially of 100% by weight of said multiconstituent fibers.

10. A nonwoven fabric laminate according to claim 1, wherein said thermally bonded nonwoven web has been formed by a procedure selected from the group consisting of carding/thermal bonding, spunbonding, wetlaying/thermal bonding, centrifugal spinning/spunbonding, wetlaying/hydroentangling/thermal bonding and carding/hydroentangling/thermal bonding.

11. A nonwoven fabric laminate according to claim 1, wherein said multiconstituent fibers are composed of a continuous phase of a polymer selected from the group consisting of polyolefins, polyamides, and polyesters.

12. A nonwoven fabric laminate according to claim 11, wherein the polymer of said continuous phase is a polyamide selected from the group consisting of nylon-6, nylon-66, nylon-11 and nylon-12.

13. A nonwoven fabric laminate according to claim 11, wherein the polymer of said continuous phase is a polyester selected from the group consisting of polyethyleneterephthalate, polybutyleneterephthalate and polytetramethyleneterephthalate.

14. A nonwoven fabric laminate according to claim 11, wherein the polymer of said continuous phases is a polyolefin selected from the group consisting of isotactic polypropylene, propylene-ethylene random copolymer, propylene-ethylene block copolymer, poly (4-methyl-1-pentene), polystyrene, and linear low density polyethylene.

15. A nonwoven fabric laminate according to claim 1, wherein one or more of the polymers which comprise said multiconstituent fiber contain a nucleating or clarifying agent selected from the group consisting of substituted-sorbitols, acrylic acid modified polypropylenes, organic acids, sodium benzoate, and stearates.

16. A nonwoven fabric laminate according to claim 1, wherein said one other web includes at least one polymer selected from polymer groups represented in said multiconstituent fibers.

17. A nonwoven fabric laminate comprising a first layer of thermoplastic filaments formed from a first thermoplastic polymer and a second layer of discrete thermoplastic fibers formed from a second thermoplastic polymer, wherein the layers are positioned in laminar surface-to-surface relationship, wherein the layers are heat bonded in discrete areas, and wherein the thermoplastic polymer in at least one of the layers is a highly dispersed blend of olefin polymers which are present as a dominant continuous phase and at least one noncontinuous phase dispersed therein, with the polymer of said noncontinuous phase or phases having a Polymer Melting Temperature (PMT) of at least 30° C. below the PMT of said continuous phase, and with the dispersed noncontinuous phase or phases occupying a substantial portion of the fiber surfaces.

18. A nonwoven fabric laminate according to claim 17, wherein said layer which is formed from a blend of olefin polymers comprises a web of discrete staple fibers.

19. A nonwoven fabric laminate according to claim 18, wherein said web of discrete staple fibers comprises a carded web of staple fibers.

20. A nonwoven fabric laminate according to claim 18, wherein said web of discrete staple fibers comprises a wetlaid web of staple fibers.

21. A nonwoven fabric laminate according to claim 17, wherein said layer which is formed from a blend of olefin polymers comprises a web of spunbonded fibers.

22. A nonwoven fabric laminate according to claim 17, wherein said first thermoplastic polymer is said blend of olefin polymers, and said second thermoplastic polymer is a meltblown polyolefin.

23. A garment comprising a nonwoven fabric laminate in accordance with claim 17.

24. A medical sterile wrap comprising a nonwoven fabric laminate in accordance with claim 17.

25. A medical garment comprising a nonwoven fabric laminate in accordance with claim 17.

26. A clean room garment comprising a nonwoven fabric laminate in accordance with claim 17.

27. A nonwoven fabric laminate comprising a first layer of thermoplastic fibers formed from a first thermoplastic polymer and a second layer of thermoplastic fibers formed from a second thermoplastic polymer wherein the layers are positioned in laminar surface-to-surface relationship, wherein the layers are heat bonded in discrete areas, and wherein at least a portion of the thermoplastic fibers in said first layer are multiconstituent fibers formed of highly dispersed blends of at least two different immiscible olefin polymers which are present as a dominant continuous phase and at least one noncontinuous phase dispersed therein, with the polymer of said noncontinuous phase or phases having a Polymer Melting Temperature (PMT) of at least 30° C. below the PMT of said continuous phase, and with the dispersed noncontinuous phase or phases occupying a substantial portion of the fiber surfaces.

28. A nonwoven fabric laminate according to claim 27, wherein the fibers of said second layer comprise meltblown fibers.

29. A nonwoven fabric laminate according to claim 27, wherein said second layer of thermoplastic fibers includes at least one polymer selected from polymer groups represented in said multiconstituent fibers.

30. A nonwoven fabric laminate comprising in sequence a first layers of thermoplastic filaments formed from a first thermoplastic polymer, a second layer of thermoplastic fibers formed from a second thermoplastic polymer, and a third layer of thermoplastic filaments formed from a third thermoplastic polymer, wherein the layers are heat bonded in discrete areas and wherein each of the first and third thermoplastic polymers is a highly dispersed blend of olefin polymers which are present as a dominant continuous phase and at least one noncontinuous phase dispersed therein, with the polymer of said noncontinuous phase or phases having a polymer melting temperature of at least 30° C. below the polymer melting temperature of said continuous phase, and with the dispersed noncontinuous phase or phases occupying a substantial portion of the fiber surfaces.

31. A nonwoven fabric laminate according to claim 30, wherein said second layer of thermoplastic fibers comprises a microfibrous layer.

32. A nonwoven fabric laminate according to claim 31, wherein said microfibrous layer comprises a layer of meltblown fibers.

33. A nonwoven fabric laminate according to claim 32, wherein said meltblown fibers comprise melt blown polypropylene fibers.

34. A nonwoven fabric laminate according to claim 33, wherein said microfibrous layer comprises a wet laid pulp layer.

35. A nonwoven fabric laminate according to claim 30, wherein said first and third layers of thermoplastic fibers each comprise a carded web of discrete staple fibers.

36. A nonwoven fabric laminate according to claim 30, wherein said first and third layers of thermoplastic fibers each comprise a web of spunbonded continuous filaments.

37. A garment comprising a nonwoven fabric laminate in accordance with claim 30.

38. A sterile wrap comprising a nonwoven fabric laminate in accordance with claim 30.

39. A medical garment comprising a nonwoven fabric laminate in accordance with claim 30.

40. A clean room garment comprising a nonwoven fabric laminate in accordance with claim 30.

41. A nonwoven fabric laminate comprising a microfibrous inner layer formed of meltblown polypropylene sandwiched between outer layers of spunbonded thermoplastic filaments, wherein the layers are positioned in laminar surface-to-surface relationship and are bonded together in discrete areas, said thermoplastic filaments of said spunbonded outer layers comprising multiconstituent filaments formed of highly dispersed blends of at least two different immiscible olefin polymers which are present as a dominant continuous phase and at least one noncontinuous phase dispersed therein, with the polymer of said noncontinuous phase or phases having a polymer melting temperature of at least 30° C. below the polymer melting temperature of said continuous phase, and with the dispersed noncontinuous phase or phases occupying a substantial portion of the fiber surfaces.

42. A nonwoven fabric laminate according to claim 41, wherein said microfibrous layer is formed of meltblown high melt flow isotactic polypropylene.

43. A nonwoven fabric laminate according to claim 41, wherein said multiconstituent filaments of said spunbonded layers comprise a polypropylene continuous phase and a polyethylene dispersed phase.

44. A nonwoven fabric laminate comprising a microfibrous inner layer formed of meltblown polypropylene sandwiched between outer layers of spunbonded thermoplastic filaments, wherein the layers are positioned in laminar surface-to-surface relationship and are heat bonded together in discrete areas, said thermoplastic filaments of said spunbonded outer layers comprising multiconstituent filaments formed of highly dispersed blends of isotactic polypropylene and linear low density polyethylene, with the polypropylene being present as a noncontinuous phase and the polyethylene being present as a noncontinuous phase dispersed therein, with the polymer of said noncontinuous phase having a polymer melting temperature of at least 30° C. below the polymer melting temperature of said continuous phase, and with the dispersed noncontinuous phase occupying a substantial portion of the fiber surfaces.

* * * * *

UNITED STATES PATENT AND TRADEMARK OFFICE
CERTIFICATE OF CORRECTION

PATENT NO. : 5,294,482
DATED : March 15, 1994
INVENTOR(S) : Scott L. Gessner

It is certified that error appears in the above-identified patent and that said Letters Patent is hereby corrected as shown below:

On the title page: [*] Notice, the disclaimer date "October 30, 2007" should be -- April 28, 2009 --.

Item: [56] References Cited, the inventor's name for U.S. Patent 4,837,067 "Govey, Jr. et al." should be -- Carey, Jr. et al. --.

Column 1, lines 42 and 43, "sight" should be -- site --.

Column 5, line 3, "each-fiber" should be -- each fiber --.

Column 6, line 9, "Of" should be -- of --.

Column 12, Table VI, "229" should be -- 228 --.

Column 13, line 34, after "least" insert -- two --.

Column 14, line 57, "phases" should be -- phase --.

UNITED STATES PATENT AND TRADEMARK OFFICE
CERTIFICATE OF CORRECTION

PATENT NO. : 5,294,482

DATED : March 15, 1994

INVENTOR(S) : Scott L. Gessner

It is certified that error appears in the above-identified patent and that said Letters Patent is hereby corrected as shown below:

Column 16, line 4, "layers" should be -- layer --.

Column 18, line 4, "noncontinuous" should be -- dominant continuous --.

Signed and Sealed this

Sixth Day of September, 1994

Attest:

BRUCE LEHMAN

Attesting Officer

Commissioner of Patents and Trademarks